United States Patent [19]

Berglund et al.

[11] Patent Number: 5,565,610
[45] Date of Patent: Oct. 15, 1996

[54] CRYSTALLINE COMPOSITION OF LYSINE AND SUCCINIC ACID OR ALKALI METAL SALT THEREOF

[75] Inventors: Kris A. Berglund, Okemos; Hasan Alizadeh, East Lansing, both of Mich.

[73] Assignee: Board of Trustees operating Michigan State University, East Lansing, Mich.

[21] Appl. No.: 546,543

[22] Filed: Oct. 20, 1995

Related U.S. Application Data

[62] Division of Ser. No. 376,395, Jan. 23, 1995.

[51] Int. Cl.⁶ .................................................. C07C 229/00
[52] U.S. Cl. ............................................................. 562/562
[58] Field of Search .............................................. 562/562

[56] References Cited

U.S. PATENT DOCUMENTS

| | | |
|---|---|---|
| 1,874,055 | 8/1932 | Liebrecht . |
| 2,824,008 | 2/1958 | Perri et al. . |
| 2,829,056 | 4/1958 | Kemmerer . |
| 3,015,567 | 1/1962 | Hause et al. . |
| 3,993,795 | 11/1976 | Mauror et al. . |
| 5,145,707 | 9/1992 | Lee . |
| 5,173,323 | 12/1992 | Omari . |
| 5,176,934 | 1/1993 | Lee . |
| 5,229,161 | 7/1993 | Turk . |
| 5,464,651 | 11/1995 | Turk .......................................... 427/64 |

FOREIGN PATENT DOCUMENTS 1154926  6/1969  United Kingdom .

*Primary Examiner*—Michael L. Shippen
*Attorney, Agent, or Firm*—Ian C. McLeod

[57] ABSTRACT

A crystalline salt of lysine hydrochloride, succinic acid or alkali metal salt, wherein the molar ratio of lysine to succinic ion calculated as succinic acid is between about 3 and 10. The salt has the appearance of ordinary table salt crystals.

5 Claims, 11 Drawing Sheets

FIG. 6
EXAMPLE 2, (2:1:1:0)

FIG. 7

SODIUM CHLORIDE

| | | |
|---|---|---|
| 2260 | 1.263 | 75.260 |
| 1670 | 1.412 | 66.200 |
| 1457 | 1.629 | 56.480 |
| 390 | 1.700 | 53.940 |
| 7637 | 1.996 | 45.440 |
| 40780 | 2.818 | 31.760 |
| 1253 | 3.250 | 27.440 |

FIG. 8

EXAMPLE 3, (2:2:1:1)

FIG. 9

FIG. 10 EXAMPLE 4, (2:2:1:1)

FIG. 11

CRYSTALLINE COMPOSITION OF LYSINE AND SUCCINIC ACID OR ALKALI METAL SALT THEREOF

This is a divisional of copending application(s) Ser. No. 0 8/ 376,395 filed on Jan. 23, 1995

BACKGROUND OF THE INVENTION (1) Field of the Invention

The present invention relates to a crystalline composition of lysine and succinic acid or an alkali metal salt of succinic acid. In particular, the present invention relates to the crystalline salt having a molar ratio of lysine to the succinic ion calculated as the acid between about 3 and 10 and to a process for preparing the crystalline composition. The crystalline composition is useful as a substitute for sodium chloride used as a table salt in foods.

(2) Description of Related Art

The prior art has described various table salt substitutes. Illustrative are U.S. Pat. Nos. 1,874,055 to Liebrecht; 2,824,008 to Petri et al; 2,829,056 to Kemmerer; 3,015,567 to Hause et al; 3,993,795 to Mauror et al; 5,145,707 to Lee; 5,173,323 to Omari; 5,176,934 to Lee and 5,229,161 to Turk. Turk describes salts of lysine and succinic acid wherein the molar ratio is 2 to 1 lysine to succinic acid which are essentially amorphous. British Patent No. 1,154,926 also describes various salts of succinic acid and lysine in a 1 to 1 mixture. The problem with these prior art salts is that they are not crystalline in form as is table salt and thus is not readily accepted on various foods such as pretzels, bagels or the like. Many substitutes also possess off flavors that are undesirable.

OBJECTS

It is therefore an object of the present invention to provide a novel lysine and succinic acid or succinic alkali metal salt composition which is crystalline in form and possesses a desirable salty flavor. Further, it is an object of the present invention to provide a process for forming the composition. These and other objects will become increasingly apparent by reference to the following description.

DESCRIPTION OF PREFERRED EMBODIMENTS

The present invention relates to a crystalline composition having the empirical formula wherein Lys is L-lysine, Succ is succinic ion and X is selected from the group consisting of a sodium ion and a potassium ion and mixtures thereof, wherein a is about 3 to 10, wherein b is approximately the same as a, c is 1 calculated as succinic acid, and d is 0 to 2.

Further the present invention relates to a process for the preparation of a crystalline composition having the empirical formula:

wherein Lys is L-lysine, Succ is succinic ion and X is selected from the group consisting of a sodium and a potassium ion and wherein a is between about 3 to 10, wherein b is approximately the same as a, c is 1 calculated as succinic acid, and d is 0 to 2 which comprises: admixing lysine hydrochloride and a succinate compound selected from the group consisting of succinic acid and alkali metal salts thereof in a molar ratio of Lys to Succ calculated as succinic acid of about 2:1 in an aqueous solution until solution is near saturation; heating the solution at a temperature between about 60° C. and 80° C. and at a reduced pressure (preferably 25 in-Hg) such that water is removed from the solution; cooling the solution so that the crystalline composition precipitates from the solution; and separating the crystalline salt from the solution, preferably by vacuum filtration.

The lysine (Lys) must be present in a molar ratio of between about 3 to 10 to succinic ion calculated as succinic acid which is important to forming the crystals. Preferably a mixture of lysine monohydrochloride and lysine monohydrate is used. The reason for this is not understood since one mole of succinic acid can form a salt with two moles of lysine as described in Turk.

The preferred alkali metal ion is potassium, since it contributes no sodium ion to the crystalline salt of the present invention. Mono- or di-alkali metal salts of succinic acid can be used. The salts are formed by reacting an alkali metal base with succinic acid.

Lysine hydrochloride, preferably as the monohydrochloride, is used as the starting material, thus contributing chloride ion to the crystalline product. The chloride ion is necessary to the formation of the crystalline composition.

The solution is heated to between about 60° C. to 80° C., preferably 70° C. and then cooled. The cooling is to about 30° C. or lower.

The salts are prepared from aqueous solutions with varying compositions. The nomenclature used to describe the solution composition is a series of molar ratios, i:j:k:l, wherein i is moles of L-lysine, j is moles of chloride ion, k is moles of succinic acid, and l is either moles of sodium or potassium.

EXAMPLE 1

Solution composition—2:1:1:0, sodium/potassium free 10 grams of L-lysine monohydrochloride and 8.95 grams of L-lysine monohydrate were dissolved in 25 ml of water.

6.5 grams of succinic acid were added and dissolved. The resulting solution was placed in a distillation unit with variable reflux. The solution was heated to 70° C. while being stirred. The temperature of solution (58° C.) and vacuum (25 mm of Hg) were maintained until about 40% of the water (10 grams) was collected as condensate. The resulting solution was cooled to room temperature resulting in crystallization. The slurry was filtered through a 5–10 micron filter; the retained solids was the crystalline product. Elemental analysis was performed on two samples of the crystalline product wherein sample 1 had twice the cooling time of sample 2 and the results are given in Table 1.

TABLE 1

Elemental analysis of Example 1. Solution composition-2:1:1:0

|  | sample 1 (wt. %) | sample 2 (wt. %) |
|---|---|---|
| carbon | 34.54 | 34.80 |
| hydrogen | 8.45 | 8.62 |
| nitrogen | 12.56 | 12.37 |
| chlorine | 14.55 | 12.93 |
| molar ratio | 10:10:1:0 | 7:7:1:0 |

Figure 2:
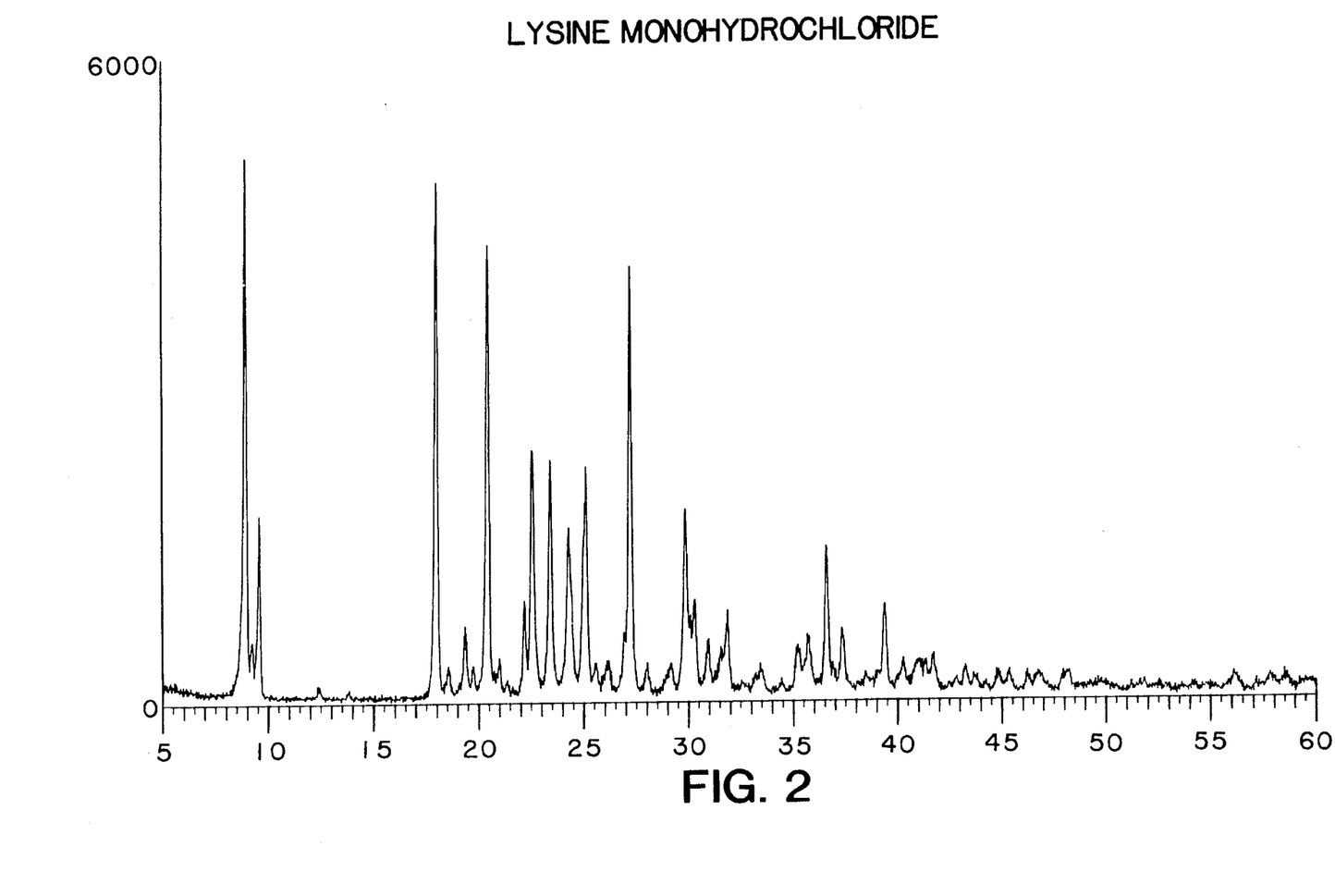
FIG. 2 is the x-ray powder diffractometry pattern of lysine monohydrochloride.
Figure 3:
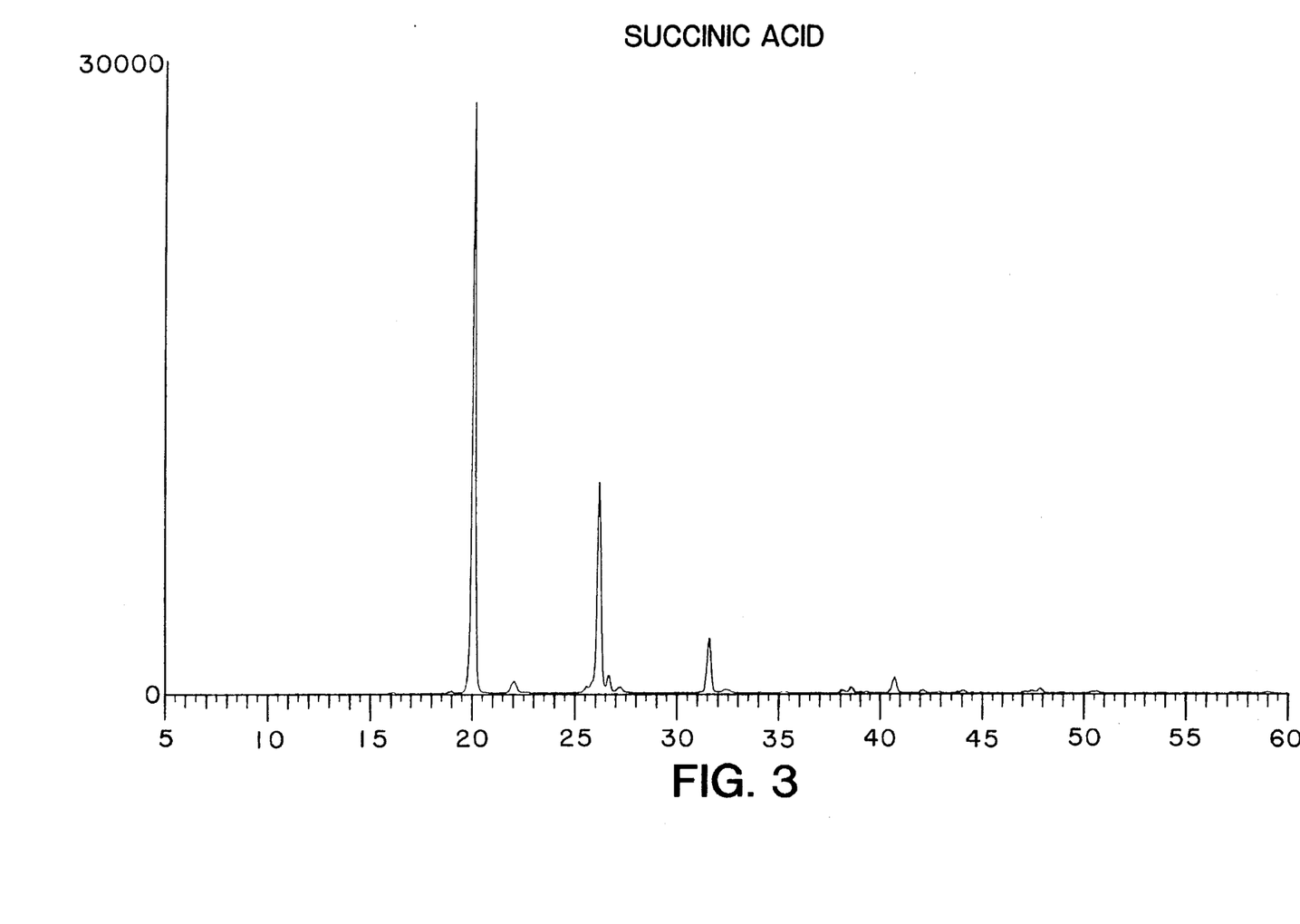
FIG. 3 is the x-ray powder diffractometry pattern of succinic acid.
Figure 4:
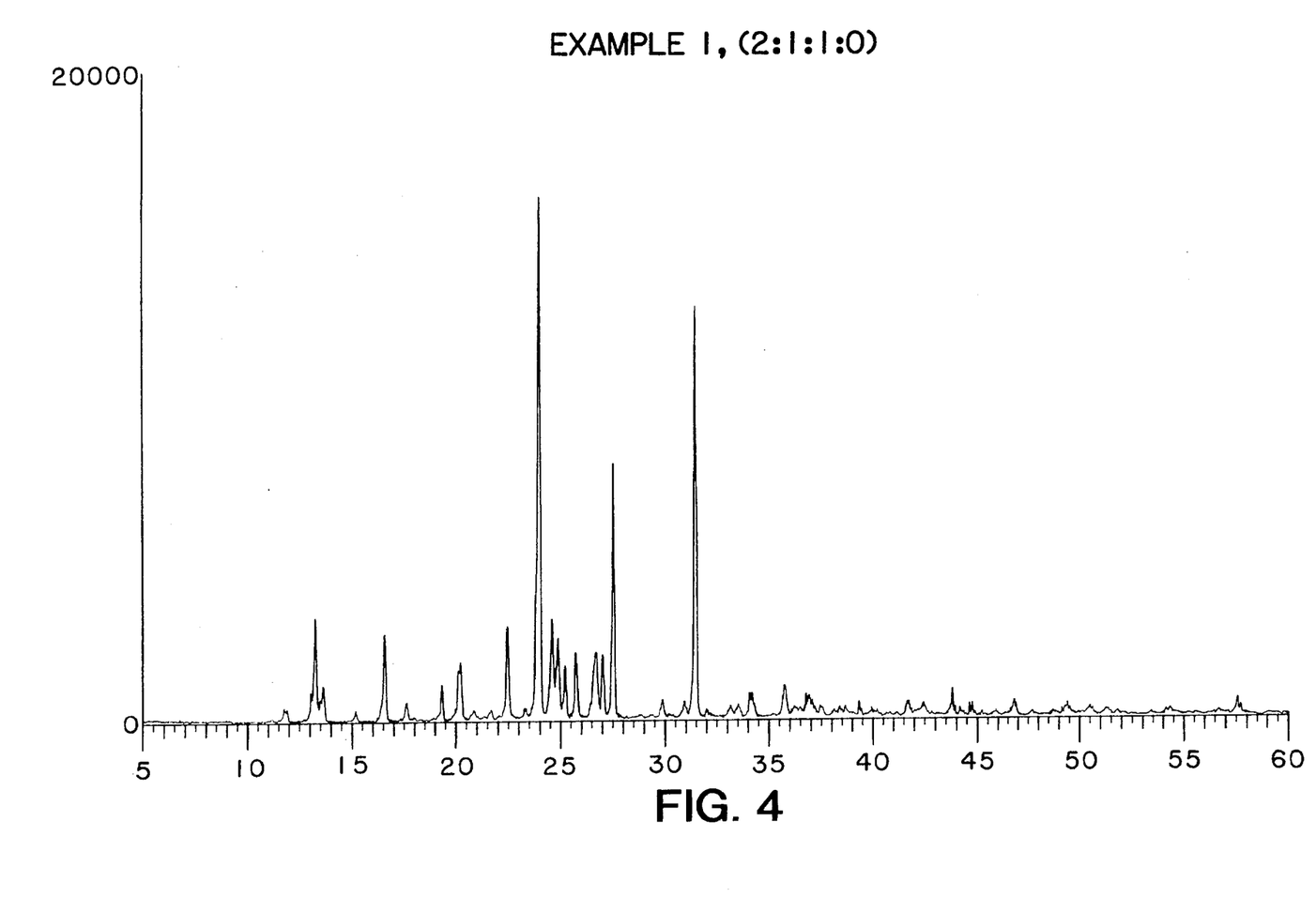
FIG. 4 is the x-ray powder diffractometry pattern of the 2:1:1:0 product of Example 1.
Figure 5:
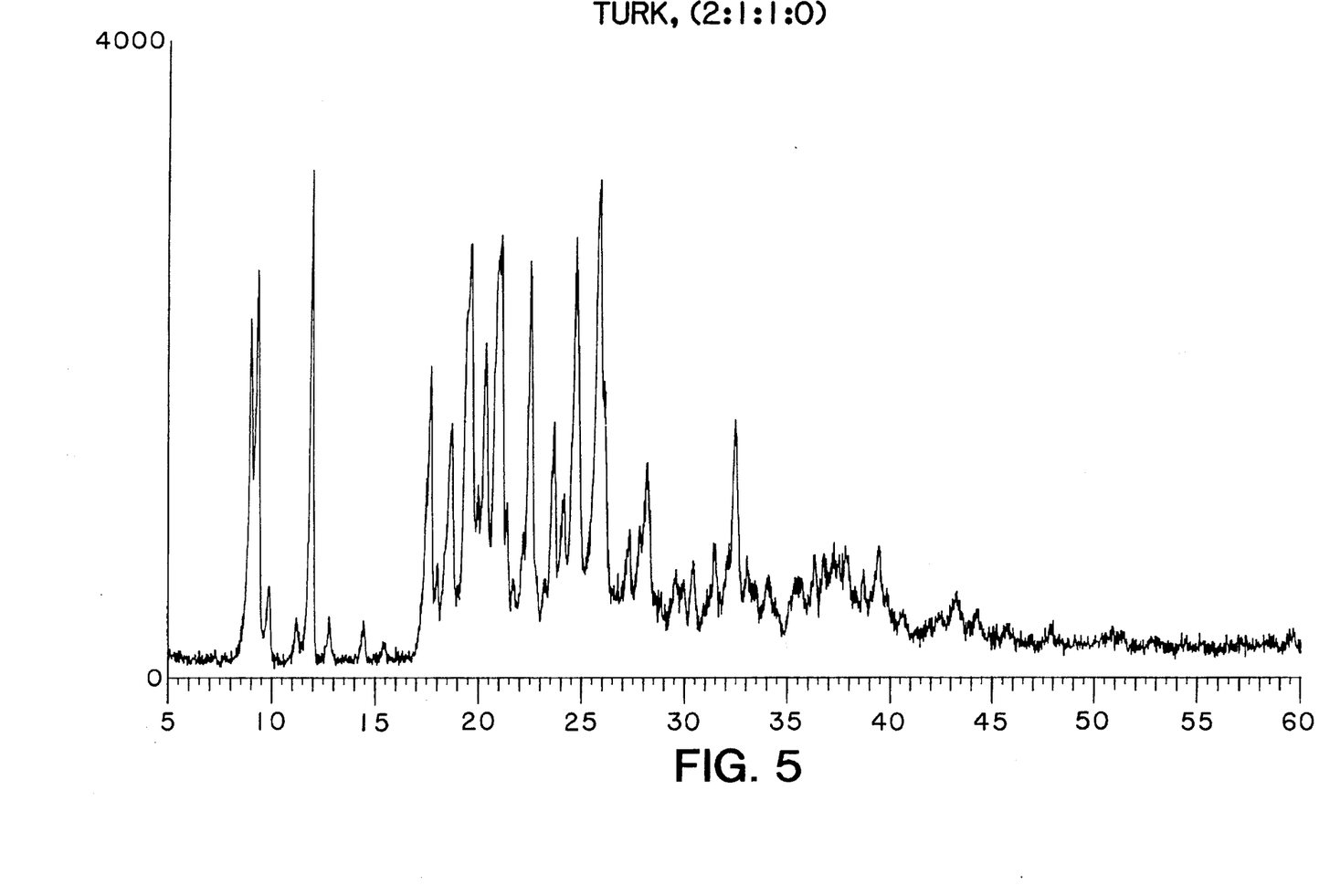
FIG. 5 is the x-ray powder diffractometry pattern of the 2:1:1:0 product of Turk.

X-ray powder diffractometry was also performed on the resulting crystalline sample and compared to samples of lysine monohydrate, lysine monohydrochloride, succinic acid, and the 2:1:1:0 example of Turk. The x-ray powder patterns of both lysine monohydrate and lysine monohydrochloride (FIGS. 1 and 2, respectively) exhibit strong reflections in the 8–10 degree region of the diffractogram. The diffractogram of succinic displays strong reflections at approximately 20 and 26 degrees (FIG. 3). The pattern obtained from the subject of the current invention is displayed in FIG. 4 and does not possess the features of the starting materials shown in FIGS. 1, 2 and 3. Furthermore, upon comparison with the pattern obtained from the 2:1:1:0 example of Turk (FIG. 5), the most intense features are not common, indicating the unique structure of the prepared crystalline material.

EXAMPLE 2

Solution composition—2:1:1:0, sodium/potassium free

Figure 6:
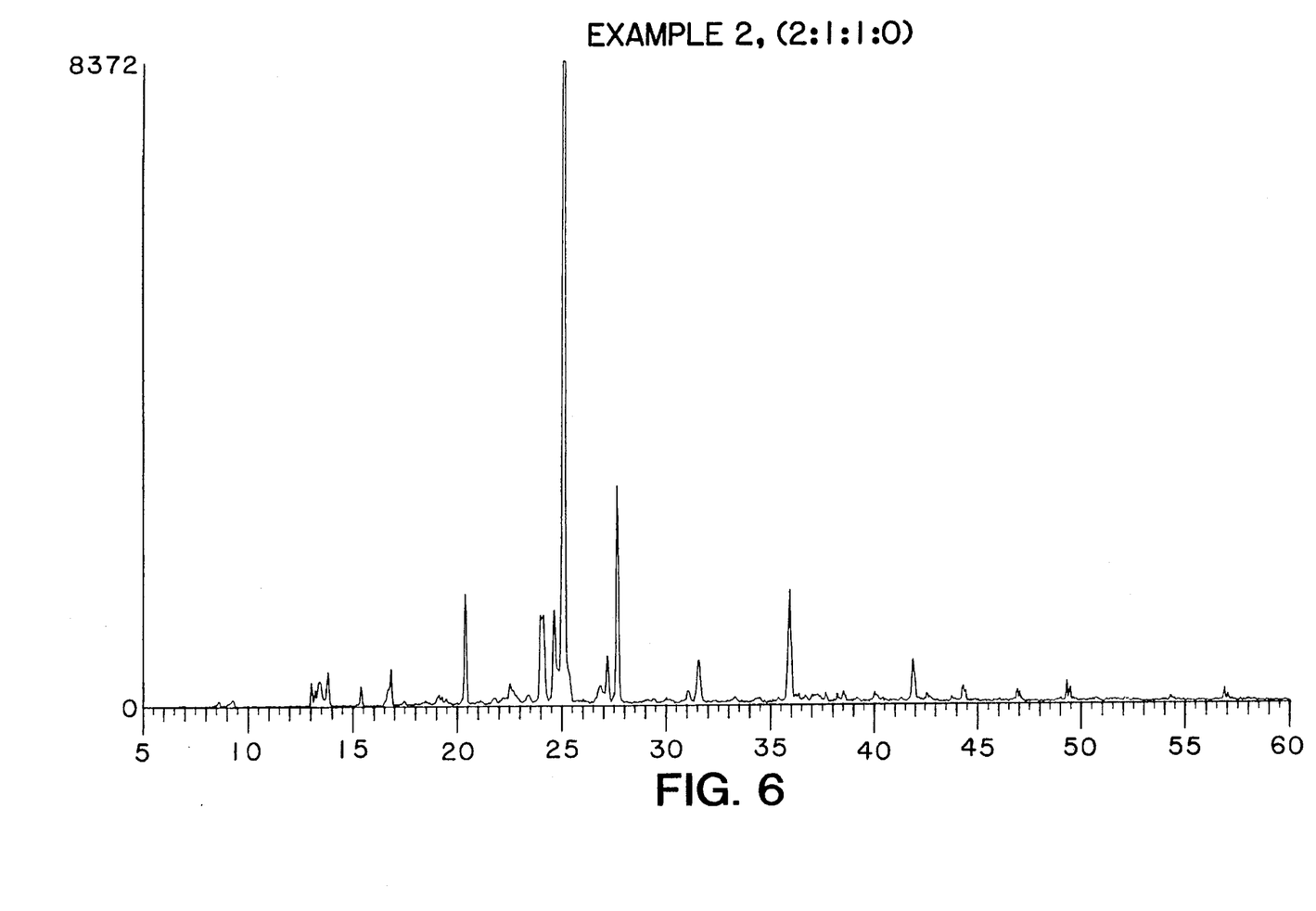
FIG. 6 is the x-ray powder diffractometry pattern of the 2:1:1:0 product of Example 2.

The same procedure as Example 1 was used with 17.9 grams of L-lysine monohydrate (0.109 moles) and 4.5 ml of concentrated hydrochloric acid (0.054 moles) instead of the two forms of lysine. A similar crystalline product was obtained and its x-ray powder pattern is shown in FIG. 6.

EXAMPLE 3

Solution composition—2:2:1:1, low sodium

The procedure was reacted as in Example 1 with 12 grams (0.073 moles) of L-lysine monohydrate dissolved in 20 ml of water to which 6.0 ml (0.073 mole) of hydrochloric acid was added. Then 2.96 grams of disodium succinate (0.018 mole) and 2.16 grams (0.018 mole) of succinic acid were added to the mixture. A crystalline product resulted with the composition shown in Table 2.

TABLE 2

Elemental analysis of Example 3 Solution composition-2:2:1:1

|  | weight % |
|---|---|
| carbon | 33.12 |
| hydrogen | 8.46 |
| nitrogen | 11.99 |
| chlorine | 15.49 |
| sodium | 1.26 |
| molar ratio | 9:9:1:1.15 |

Figure 1:
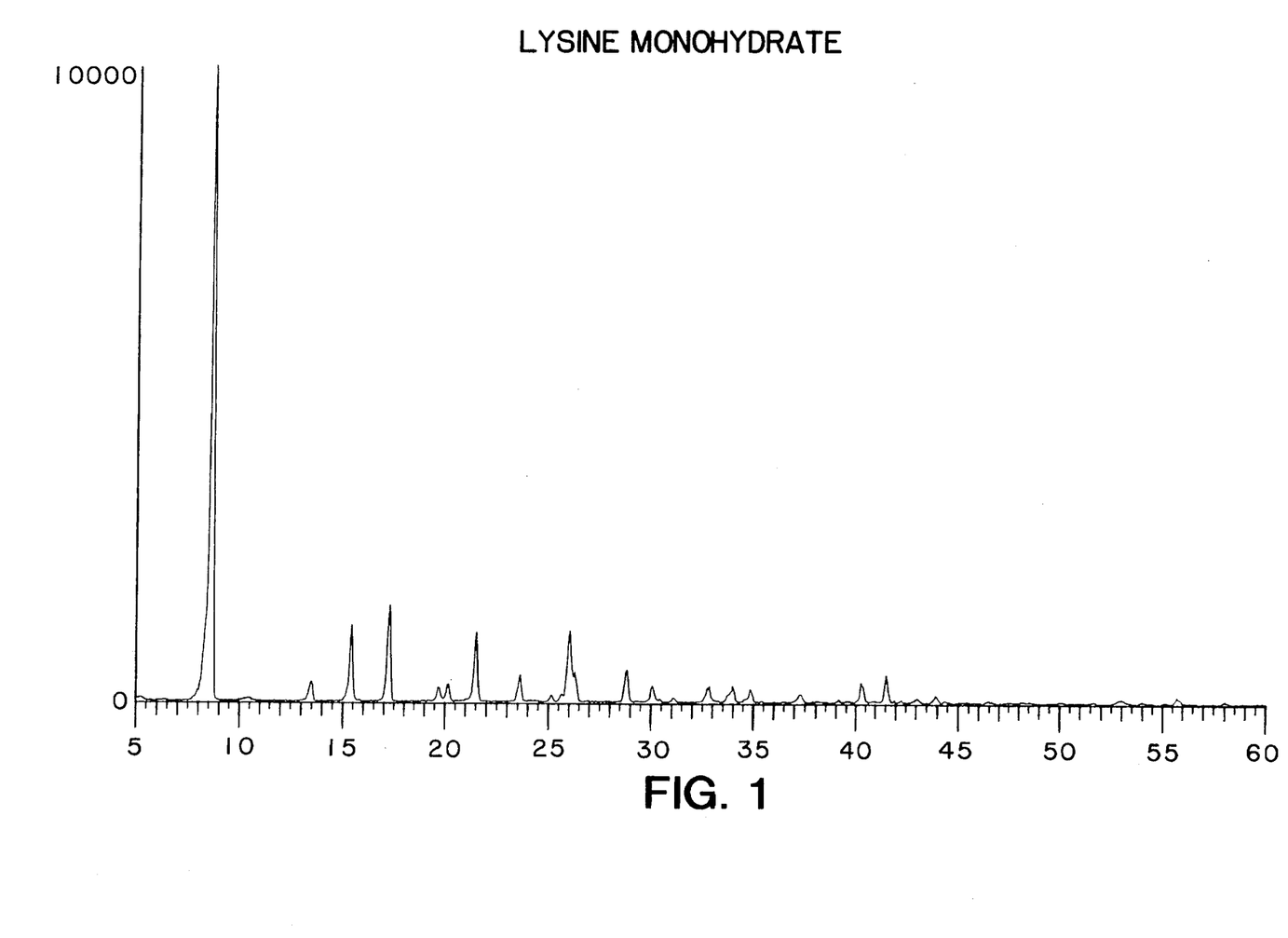
FIG. 1 is the x-ray powder diffractometry pattern of lysine monohydrate.
Figure 7:
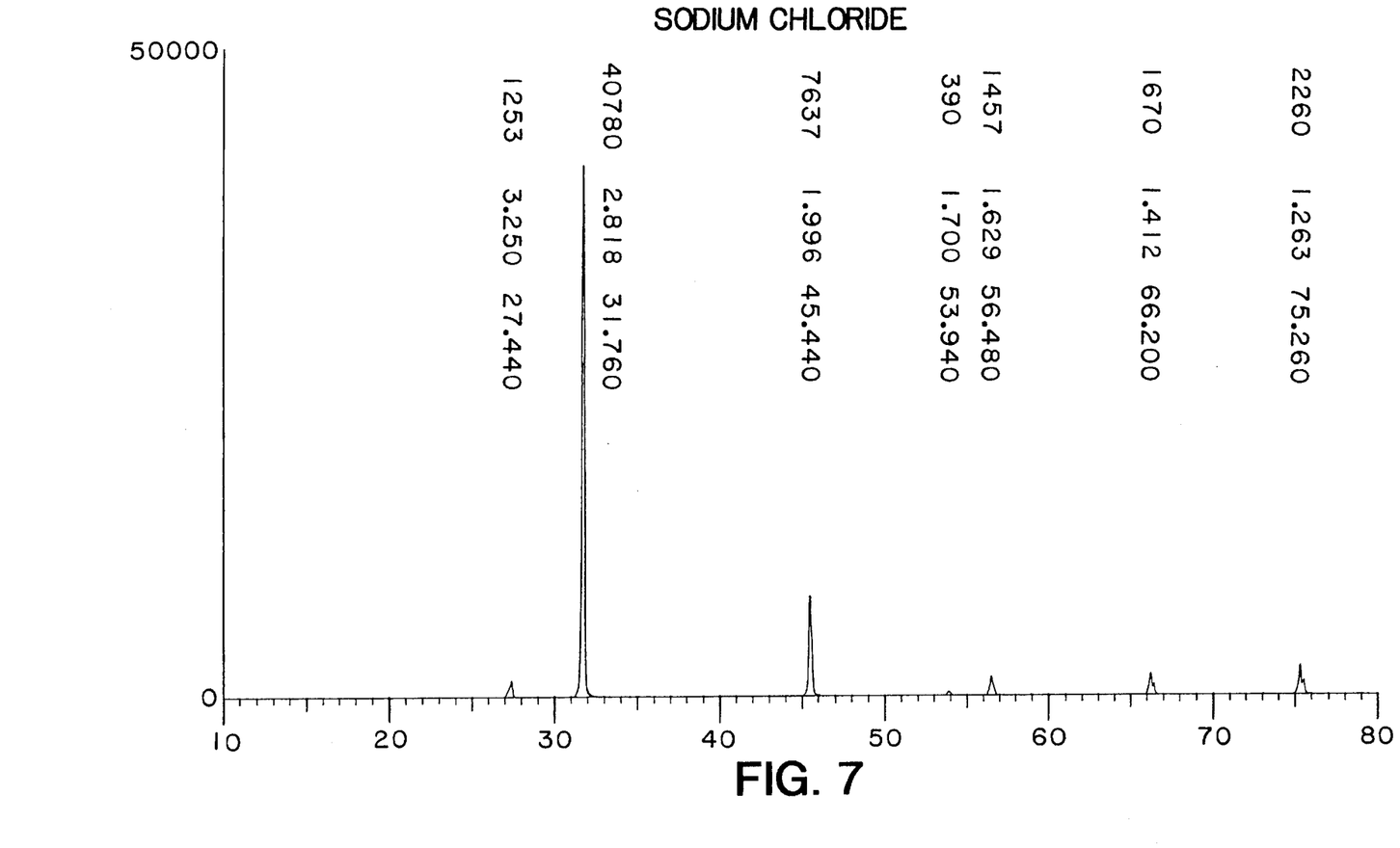
FIG. 7 is the x-ray powder diffractometry pattern of sodium chloride.
Figure 8:
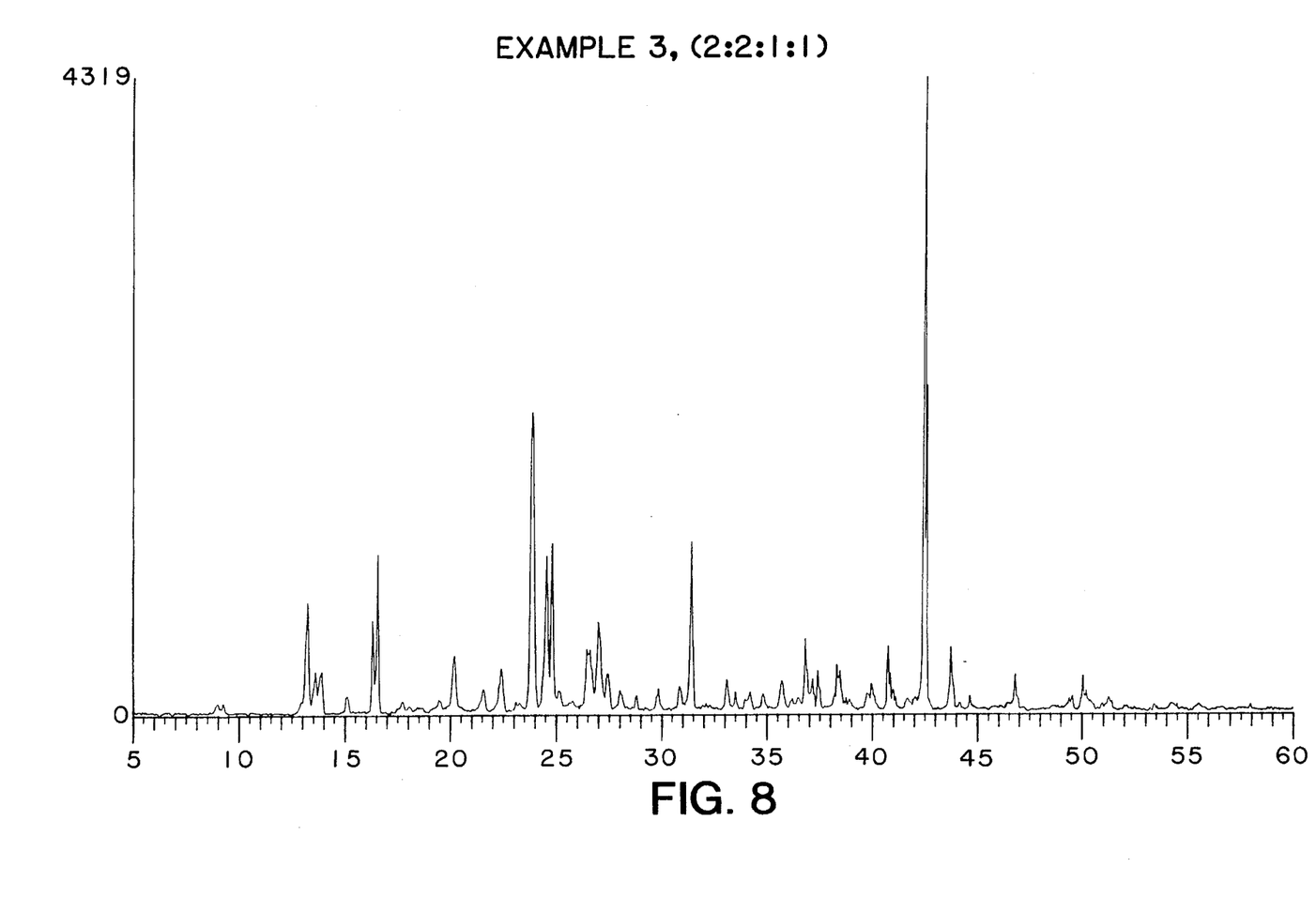
FIG. 8 is the x-ray powder diffractometry pattern of the 2:2:1:1 product of Example 3.
Figure 9:
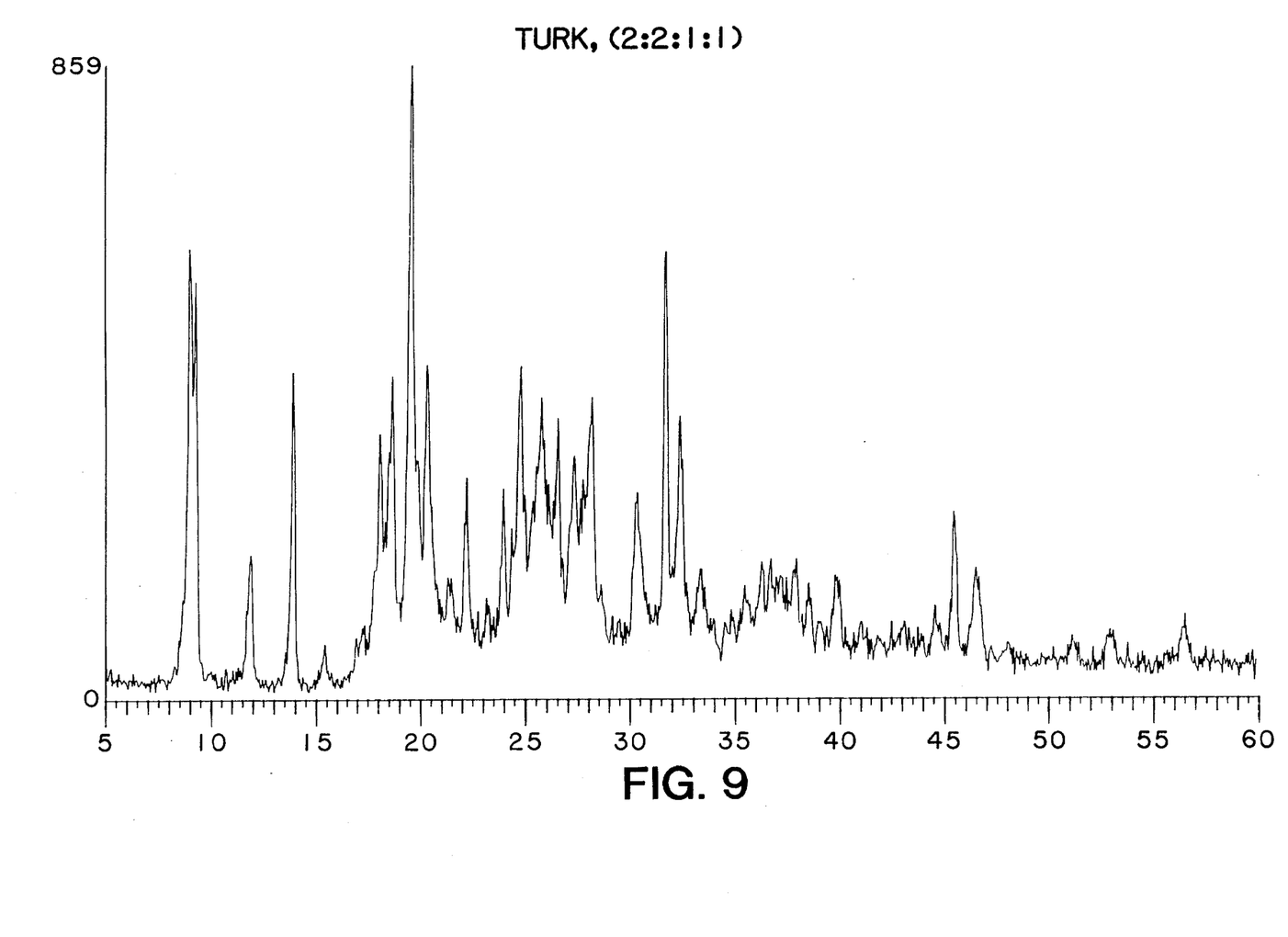
FIG. 9 is the x-ray powder diffractometry pattern of the 2:2:1:1 product of Turk.

X-ray powder patterns were collected for crystalline sodium chloride, the current example, and example 2:2:1:1 of Turk (FIGS. 7, 8 and 9, respectively). The current example did not display features of the starting materials as shown in FIGS. 1, 2 and 3 nor does it possess a common diffractogram with the example of Turk. It should also be noted that the sodium content is only 1.26%.

EXAMPLE 4

Solution composition—2:2:1:1, low potassium

Figure 10:
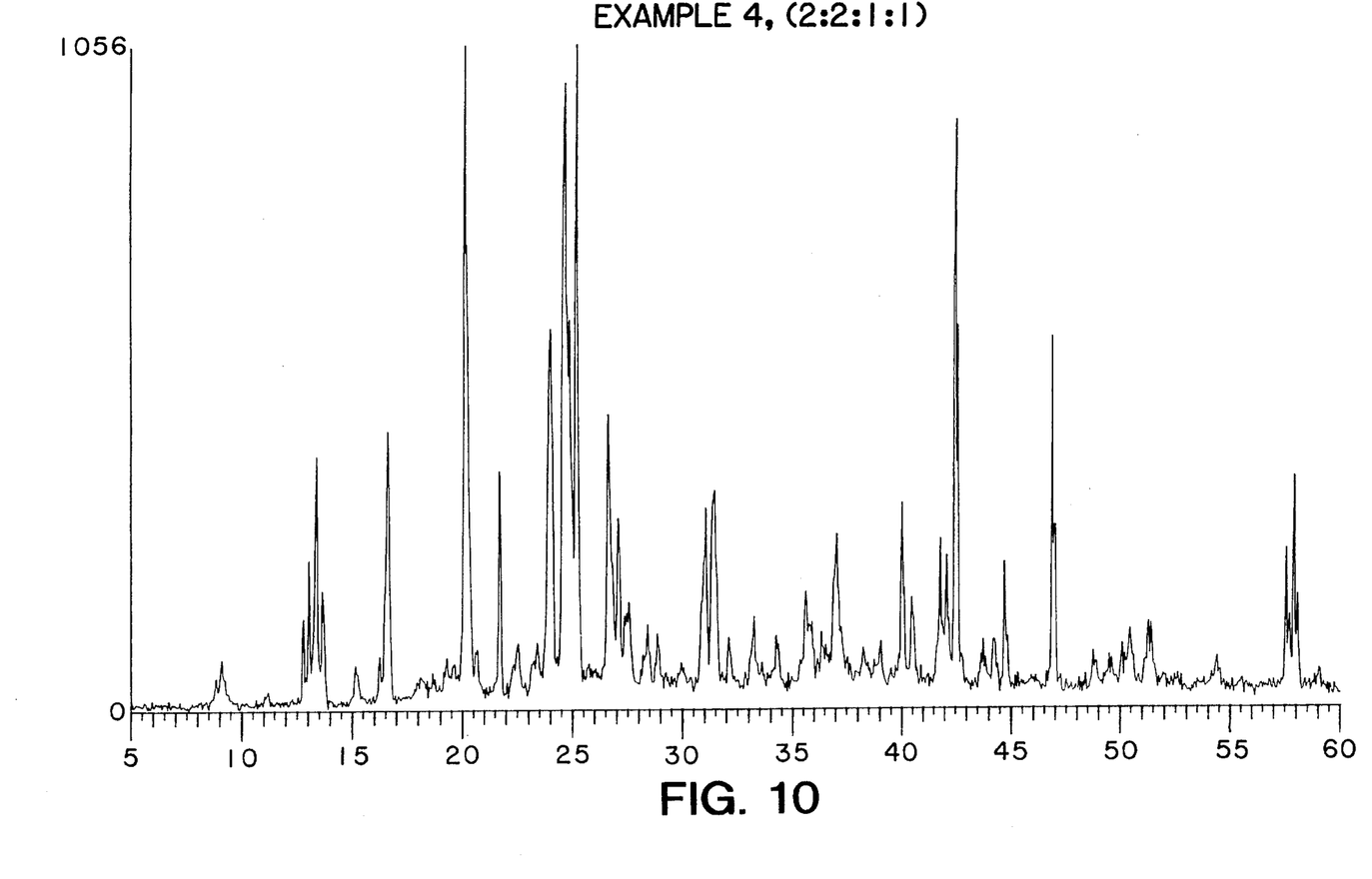
FIG. 10 is the x-ray powder diffractometry pattern of the 2:2:1:1 product of Example 4.

The same procedure was used as in Example 3 except the 2.94 grams (0.018 mole) of disodium succinate were replaced by 2.05 grams (0.036 mole) of potassium hydroxide. A similar crystalline product was obtained with its powder pattern shown in FIG. 10.

EXAMPLE 5

Solution composition—4:3:2:1, low potassium

Figure 11:
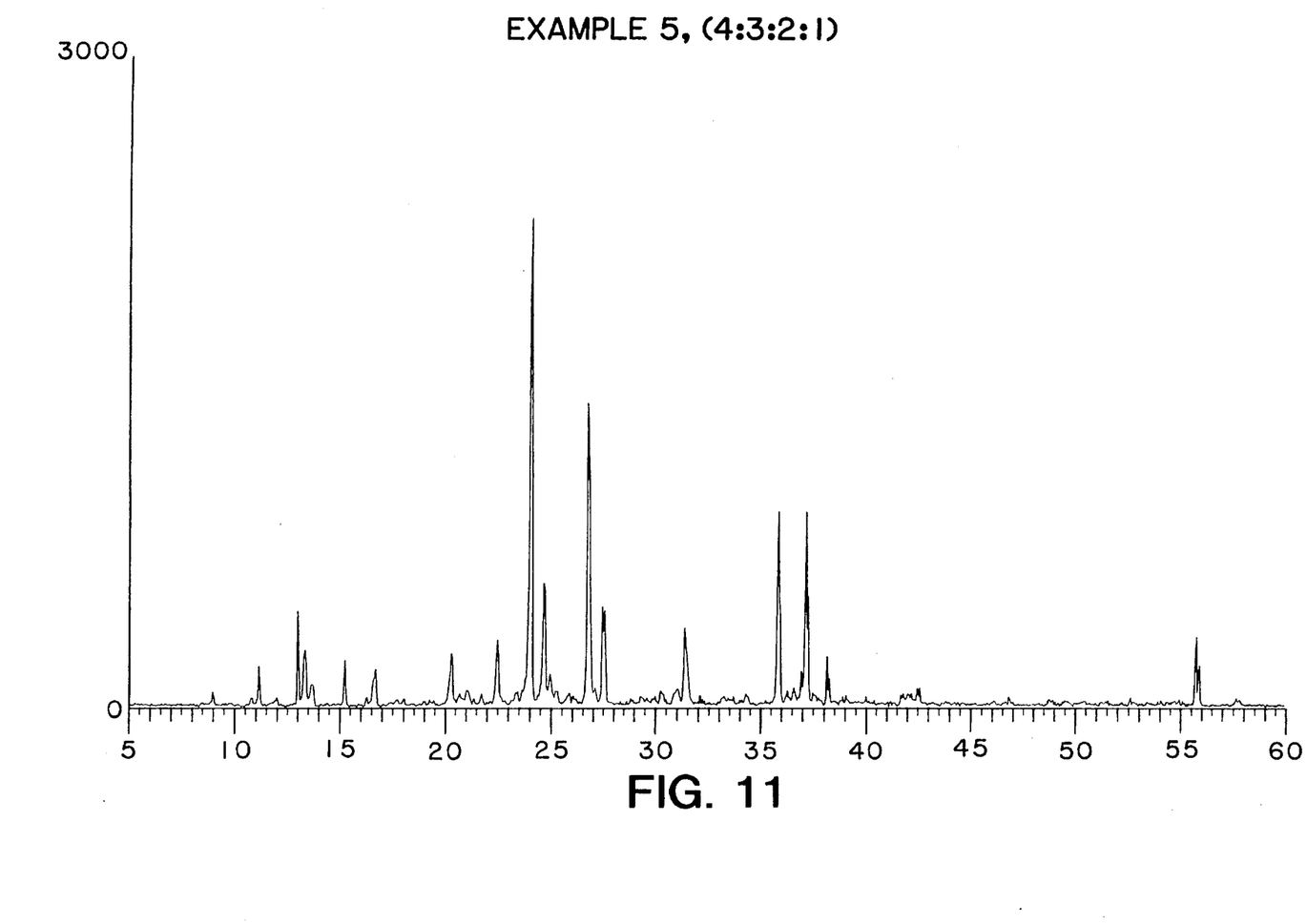
FIG. 11 is the x-ray powder diffractometry pattern of the 4:3:2:1 product of Example 5.

The same procedure was used as in Example 1 except 2.04 grams (0.027 mole) of potassium chloride were added. A similar crystalline product was obtained with its elemental analysis given in Table 3 and its x-ray powder given in FIG. 11.

TABLE 3

Elemental analysis of Example 4 solution composition-4:3:2:1

|  | weight % |
|---|---|
| carbon | 33.57 |
| hydrogen | 8.60 |
| nitrogen | 11.89 |
| chlorine | 13.77 |
| potassium | 1.45 |
| molar ratio | 7:7:1:0.6 |

EXAMPLE 6

Mixtures of potassium chloride with Example 1 salt product.

Potassium chloride is often used as a salty flavor to replace sodium chloride. Unfortunately, potassium chloride has a strong metallic taste. Therefore, experiments were conducted to determine if the salty flavor of the current invention could be used to mask the metallic flavor of the potassium ion. Mixtures of potassium chloride and Example 1 with varying weight percent were prepared by grinding.

The 2 to 5 wt% of KCl and Example 1 gave the best salty taste. KCl concentrations lower than 2% have little effect on the salty flavor, while higher concentrations increased the metallic taste. The results of this taste trials are presented in

TABLE 4

Taste trials of KCl mixtures with Example 1 salt product at different wt % concentrations.

| Wt % KCl/Ex. 1 | Powder taste |
| --- | --- |
| 100 | Irritates tongue |
| 0 | Salty |
| 2 | Saltier |
| 5 | Saltier |
| 10 | Metallic-salty |
| 32 | Metallic-salty |

EXAMPLE 7

Comparison of the taste of different Examples of salts of present invention with one another and with other existing salt products.

The salts of present invention and prior ones were tasted as solids and solutions in water. Example 1 salt solution concentrations of 4 to 70 wt% were tasted and 15 wt% solution found to best represent the salty taste. Therefore, 15 wt% solutions of different salt products were prepared, tasted, and compared.

The solid and solution tastes of similar salts appeared to be the same, but the solution gives a milder taste at 15 wt% concentration.

In summary, Examples 1 and 2 (Example 1 having better taste of salt than Example 2) of the present invention with the same solution composition resembles sodium chloride better than that of Turk. Example 3 of low sodium tastes better than any other examples of salt products containing sodium or potassium. The summary of taste trial of different salt products are presented in Table 5.

TABLE 5

Summary of taste trials of different salt products

| Salt product | Molar ratio* | Taste* |
| --- | --- | --- |
| Table salt | N/A | Saltiest |
| Turk | 2:2:1:1 | Saltier+ |
| Turk | 2:1:1:0 | Less salty |
| Ex. 1 | 2:1:1:0 | Salty+ |
| Ex. 2 | 2:1:1:0 | Salty |
| Ex. 3 | 2:2:1:1 | Saltier+ |
| Ex. 4 | 2:2:1:1 | Saltier |
| Ex. 5 | 4:3:2:1 | Saltier |
| Ex. 6 | 2:1:1:1 | Saltier |

*Aqueous starting solution composition molar ratios of Lys:Cl:Succ:Na or K.
**Salty+, tastes better than salty.

It is intended that the foregoing description be only illustrative of the present invention and that the present invention be limited only by the hereinafter appended claims.

We claim:

1. A crystalline composition having the empirical formula $$Lys_a Cl_b Succ_c X_d$$

wherein Lys is L-lysine, Succ is succinic ion and X is selected from the group consisting of a sodium ion and a potassium ion and mixtures thereof, wherein a is about 3 to 10, b is approximately the same as 1, c is 1 calculated as succinic acid, d is 0 to 2.

2. The composition of claim 1 wherein d is 1.15 and X is sodium ion.

3. The composition of claim 1 wherein d is 0.6 and X is potassium ion.

4. The composition of claim 1 wherein X is hydrogen ion.

5. The composition of claim 1 wherein X is sodium and potassium.

\* \* \* \* \*